United States Patent
Uchida (10) Patent No.: US 10,849,494 B2
(45) Date of Patent: Dec. 1, 2020

(54) OPTICAL COHERENCE TOMOGRAPHY APPARATUS, IMAGE PROCESSING APPARATUS, IMAGE PROCESSING METHOD, AND STORAGE MEDIUM

(71) Applicant: CANON KABUSHIKI KAISHA, Tokyo (JP)

(72) Inventor: Hiroki Uchida, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 151 days.

(21) Appl. No.: 16/113,820

(22) Filed: Aug. 27, 2018

(65) Prior Publication Data
US 2019/0069774 A1 Mar. 7, 2019

(30) Foreign Application Priority Data
Sep. 4, 2017 (JP) ................ 2017-169295

(51) Int. Cl.
*A61B 3/14* (2006.01)
*A61B 3/10* (2006.01)
*A61B 3/00* (2006.01)
*A61B 3/12* (2006.01)

(52) U.S. Cl.
CPC ............ *A61B 3/102* (2013.01); *A61B 3/0025* (2013.01); *A61B 3/1225* (2013.01)

(58) Field of Classification Search
CPC ..... A61B 3/102; A61B 3/0025; A61B 3/0058; A61B 3/14; A61B 5/0066
USPC ........................................ 351/206
See application file for complete search history.

(56) References Cited

FOREIGN PATENT DOCUMENTS

JP 2015-131107 A 7/2015
JP 2016047100 A * 4/2016

* cited by examiner

*Primary Examiner* — Mahidere S Sahle
(74) *Attorney, Agent, or Firm* — Canon U.S.A., Inc. IP Division (57) ABSTRACT

An apparatus includes an interference optical system configured to acquire a tomographic image of an eye by using interference light between return light from the eye irradiated with measurement light and reference light corresponding to the measurement light, a determination unit configured to determine, by using at least one of information about an acquisition time for acquiring the tomographic image and information about an imaging view angle of the tomographic image, a search range for searching for a position corresponding to a first tomographic image of the eye, the position being in a second tomographic image of the eye, and the second tomographic image having been acquired at a time different from a time when the first tomographic image is acquired, and a registration unit configured to perform registration of the first tomographic image and the second tomographic image by using information about the determined search range.

13 Claims, 6 Drawing Sheets

OPTICAL COHERENCE TOMOGRAPHY APPARATUS, IMAGE PROCESSING APPARATUS, IMAGE PROCESSING METHOD, AND STORAGE MEDIUM

BACKGROUND

Field of the Disclosure

The present disclosure relates to an optical coherence tomography apparatus, an image processing apparatus, an image processing method, and a storage medium.

Description of the Related Art

Apparatuses using Optical Coherence Tomography (hereinafter referred to as "OCT") as a method for nondestructively and noninvasively acquiring tomographic images of a measurement object, such as a living body, are in practical use. The OCT is widely used for ophthalmic apparatuses to acquire images for ophthalmic diagnosis.

In the OCT, light reflected from a measurement object and light reflected from a reference mirror are allowed to interfere with each other and the intensity of interference light is analyzed to thereby obtain tomographic images of the measurement object. As the OCT, time-domain OCT for obtaining depth information about the measurement object by sequentially changing the position of the reference mirror, spectral domain optical coherence tomography (SD-OCT) for dividing interference light obtained by allowing light to interfere using low-coherence light and obtaining depth information by replacing the light by frequency information, and swept source optical coherence tomography (SS-OCT) using a swept source light source to disperse a wavelength of light to be output are known. The SD-OCT and the SS-OCT are also collectively referred to as Fourier domain optical coherence tomography (FD-OCT).

In recent years, angiography which uses the OCT methods as described above and does not use any contrast medium has been proposed. The angiography is referred to as OCT angiography (hereinafter referred to as "OCTA"). In the OCTA, acquired three-dimensional motion contrast data is integrated in a depth direction and is projected on a two-dimensional plane, thereby generating a planar blood vessel image (hereinafter also referred to as an "OCTA image"). The motion contrast data described herein refers to data obtained by repeatedly capturing images of the same cross-section and detecting a time variation in a subject during the image capturing. This data is obtained by, for example, calculating a phase difference or vector difference of a complex OCT signal, or a time variation in the intensity of the complex OCT signal, as discussed in Japanese Patent Application Laid-Open No. 2015-131107.

SUMMARY

According to an aspect of the present invention, an optical coherence tomography apparatus includes an interference optical system configured to acquire a tomographic image of an eye by using interference light between return light from the eye irradiated with measurement light and reference light corresponding to the measurement light, a determination unit configured to determine, by using at least one of information about an acquisition time for acquiring the tomographic image and information about an imaging view angle of the tomographic image, a search range for searching for a position corresponding to a first tomographic image of the eye, the position being in a second tomographic image of the eye, and the second tomographic image having been acquired at a time different from a time when the first tomographic image is acquired, and a registration unit configured to perform registration of the first tomographic image and the second tomographic image by using information about the determined search range.

Further features of the present invention will become apparent from the following description of exemplary embodiments with reference to the attached drawings.

DESCRIPTION OF THE EMBODIMENTS

The present invention will be described in detail below based on exemplary embodiments. The following exemplary embodiments do not limit the present invention related to the claims and not all the combinations of features described in the exemplary embodiments are necessarily essential to means for solving the issue targeted to be solved by the present invention. The following exemplary embodiments illustrate optical coherence Tomography (OCT) angiography (hereinafter referred to as "OCTA"). However, the present invention can also be applied to, for example, general OCTs. The following exemplary embodiments illustrate a case where a difference value or the like between a plurality of tomographic images is obtained. However, the present invention can also be applied to, for example, a case where one tomographic image is generated by combining (averaging) a plurality of tomographic images. In other words, the present invention can be applied as long as registration between a plurality of tomographic images is performed. More preferably, the present invention is applied to a case where registration between a plurality of tomographic images obtained by controlling measurement light so that a substantially same position is repeatedly scanned with the measurement light.

In the OCTA, a plurality of tomographic images is successively acquired at the same scanning position and, for example, a difference value between the plurality of tomographic images is obtained, thereby obtaining motion contrast data corresponding to a blood flow. Accordingly, there is a need to acquire a plurality of tomographic images through scanning exactly at the same position. An acquisition time for successively acquiring a plurality of tomographic images is about several milliseconds to several tens of milliseconds, which is a relatively short time. However, a small positional deviation may occur between the plurality of tomographic images due to a motion of the face or eyes of an examinee. In a case where a small positional deviation occurs between the tomographic images, a difference value or the like between the tomographic images becomes larger than the original value, so that an artifact, such as a white line, appears on an OCTA image.

In the OCT of the related art, for example, a method for correcting a positional deviation between tomographic images through post processing has been used as a method for correcting a positional deviation between tomographic images as described above. In such a case, in template matching, which is mainly used, an extremely large search range enables correction of a large positional deviation, but may cause an increase in time required for calculating the positional deviation. On the other hand, if the search range is extremely small, the time required for calculating the positional deviation can be reduced, but there is a possibility that a large positional deviation cannot be corrected. In such a case, since a moving amount of an eye to be examined varies depending on an acquisition time for acquiring tomographic images and the like, the size of a search range for achieving both an appropriate positional deviation correction and an appropriate positional deviation calculation time also varies.

Accordingly, the present exemplary embodiment is directed to achieving an appropriate positional deviation correction and an appropriate positional deviation calculation time.

In this case, according to an exemplary embodiment of the present invention, a search range for performing registration of a plurality of tomographic images can be determined using information about an acquisition time for acquiring tomographic images (e.g., in consideration of the acquisition time for acquiring tomographic images). Accordingly, it is possible to perform registration of a plurality of tomographic images by using information about the determined search range (e.g., four coordinate positions representing a rectangular region as a part of a certain tomographic image). Consequently, it is possible to achieve both an appropriate positional deviation correction and an appropriate positional deviation calculation time.

The information about the acquisition time for acquiring tomographic images described herein refers to, for example, an acquisition time interval for acquiring a plurality of tomographic images. The acquisition time interval for acquiring a plurality of tomographic images refers to, for example, an acquisition time for acquiring one tomographic image in a case where a tomographic image is acquired in each of a forward path and a backward path for reciprocating scanning by a scanning unit. Moreover, the acquisition time interval refers to, for example, an interval between acquisitions of two successive tomographic images in a case where a tomographic image is acquired in the forward path for reciprocating scanning by the scanning unit and no tomographic image is acquired in the backward path for reciprocating scanning by the scanning unit In this case, the acquisition time interval includes a travel time of the scanning unit from an end of one main scanning operation to a start of a subsequent main scanning operation. As the acquisition time interval becomes longer, the moving amount of the eye to be examined may become larger. Accordingly, when the acquisition time interval is long, it is desirable to set a larger search range. In this case, a central position of the search range may be set at the same position or different positions. Additionally, even in a case where the acquisition time interval is long, there is no need to always set a larger search range. Specifically, in a case where the acquisition time interval is longer than at least one of predetermined acquisition time intervals that are set stepwise, the search range may be set so as to gradually increase. In other words, it is only required that in a second acquisition time interval longer than a first acquisition time interval, a second search range larger than a first search range corresponding to the first acquisition time interval is set.

The acquisition time interval for acquiring a plurality of tomographic images is determined depending on, for example, the number of pieces of A-scan data on one tomographic image. Accordingly, the information about the acquisition time interval for acquiring tomographic images refers to, for example, the number of A-scan data on one tomographic image. In this case, as the number of pieces of A-scan data on one tomographic image increases, the acquisition time interval for acquiring a plurality of tomographic images may increase and the moving amount of the eye to be examined may increase. Thus, it is desirable to set a larger search range. Further, the acquisition time interval for acquiring a plurality of tomographic images is determined not only depending on the number of pieces of A-scan data on one tomographic image, but also depending on, for example, a readout rate of a line sensor in spectral domain optical coherence tomography (SD-OCT), or a swept source rate of a swept source light source in swept source optical coherence tomography (SS-OCT). In this case, as the readout rate of the line sensor (or the swept source rate of the swept source light source) decreases, the acquisition time interval for acquiring a plurality of tomographic images may increase and the moving amount of the eye to be examined may increase. Thus, it is desirable to set a larger search range.

Here, the number of pieces of A-scan data on one tomographic image is determined depending on a scanning rate and a scanning angle (an imaging view angle for one tomographic image) of the scanning unit that scans the eye to be examined with measurement light. Accordingly, the information about the acquisition time for acquiring tomographic images refers to, for example, the scanning rate and scanning angle of the scanning unit. In a case where the scanning angle is constant, as the scanning rate is increased, the number of pieces of A-scan data on one tomographic image decreases. On the other hand, as the scanning rate is reduced, the number of pieces of A-scan data on one tomographic image increases. In a case where the scanning rate is constant, as the scanning angle is increased, the number of pieces of A-scan data on one tomographic image increases. On the other hand, as the scanning angle is reduced, the number of pieces of A-scan data on one tomographic image decreases.

Depending on the setting of the scanning rate and scanning angle of the scanning unit, the acquisition time for acquiring one tomographic image can be set so as not to be changed (or so as to be shortened) even with a larger imaging view angle for one tomographic image being set. In such a setting, the inclination of the eye to be examined in the tomographic image may increase depending on the position at which an anterior eye position is irradiated with measurement light, due to a motion of the eye to be examined during imaging. Accordingly, even if the acquisition time for acquiring tomographic images is not changed (or is shortened), it is desirable to set a search range for performing registration using information about the imaging view angle of one tomographic image (e.g., the scanning angle of the scanning unit). In such a case, as described below, it is desirable to set a plurality of regions elongated in a depth direction and to perform registration in the depth direction for each region. Thus, in the case of successively acquiring a plurality of tomographic images, even in a case where the inclination of the eye to be examined in the tomographic images increases, the inclination can be corrected.

Figure 1:
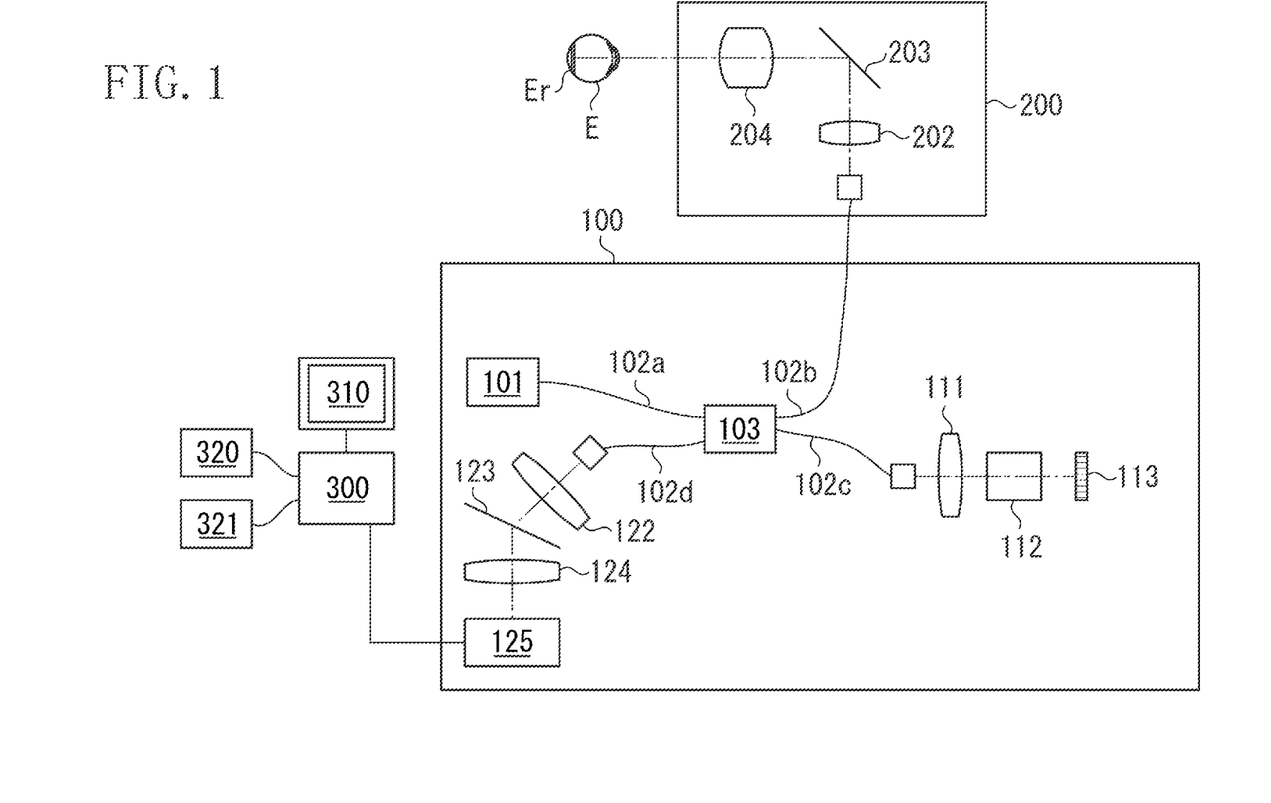
FIG. 1 illustrates a schematic configuration of an optical coherence tomography apparatus according to an exemplary embodiment of the present invention.

Next, a first exemplary embodiment of the present invention will be described below with accompanying drawings. FIG. 1 illustrates a schematic configuration of an optical coherence tomography apparatus according to the present exemplary embodiment. An optical coherence unit (interference optical system) 100 illustrated in FIG. 1 includes components described below. A low-coherence light source 101 emits near-infrared light. The light emitted from the light source 101 propagates through an optical fiber 102a. A light split unit 103 splits the light into measurement light and reference light. The measurement light split by the light split unit 103 enters an optical fiber 102b and is guided to a scanning optical system 200. The reference light split by the light split unit 103 enters an optical fiber 102c and is guided to a reflection mirror 113. Further, the reference light which has entered the optical fiber 102c is output from an end of the optical fiber 102c, passes through a collimate optical system 111, and is then incident on a dispersion compensation optical system 112 and guided to the reflection mirror 113. The reference light reflected by the reflection mirror 113 travels along the optical path in reverse and enters the optical fiber 102c again. The dispersion compensation optical system 112 corrects the dispersion of the scanning optical system 200 and the optical system in an eye E to be examined, which is a measured object. The reflection mirror 113 is configured so as to be driven in an optical axis direction by an optical path length control unit 114 (not illustrated) and is capable of changing the optical path length of the reference light relatively to the optical path length of the measurement light. Meanwhile, the measurement light that has entered the optical fiber 102b is output from an end of the optical fiber 102b. The light source 101 and the optical path length control unit 114 are controlled by a control unit 130 (not illustrated). Next, the scanning optical system 200 will be described. The scanning optical system 200 is an optical system configured to be movable relatively to the eye E to be examined. A drive control unit 205 (not illustrated) of the scanning optical system 200 is configured to be capable of driving the scanning optical system 200 in a back-and-forth direction, an up-and-down direction, or a left-and-right direction with respect to the eye axis of the eye E to be examined, thus enabling alignment of the scanning optical system 200 with respect to the eye E to be examined. The light output from the end of the optical fiber 102b is substantially collimated by an optical system 202 and is then incident on a scanning unit 203. The scanning unit 203 includes two galvanometer mirrors each capable of rotating a mirror surface. One of the galvanometer mirrors deflects light in a horizontal direction, and the other one of the galvanometer mirrors deflects light in the vertical direction. Thus, the scanning unit 203 deflects the incident light under the control of the drive control unit 205. This configuration enables the scanning unit 203 to scan, with the measurement light, a fundus Er of the eye E to be examined in two directions, a main scanning direction along the plane of FIG. 1 and a sub-scanning direction perpendicular to the plane of FIG. 1. The light with which the scanning unit 203 performs scanning passes through a lens 204 and forms an illumination spot on the fundus Er of the eye E to be examined. The illumination spot moves (scans) along the fundus Er of the eye E to be examined in response to the in-plane deflection by the scanning unit 203. The light reflected at the illumination spot position travels along the optical path in reverse, enters the optical fiber 102b, and returns to the light split unit 103.

As described above, the reference light reflected by the reflection mirror 113 and the measurement light reflected by the fundus Er of the eye E to be examined return to the light split unit 103 as return light, and interfere with each other so that interference light is generated. The interference light passes through an optical fiber 102d and is emitted toward a lens 122. Then, the interference light is substantially collimated and incident on a diffraction grating 123. The diffraction grating 123 has a periodic structure and disperses the interference light incident thereon. The dispersed interference light forms an image on a line sensor 125 through an image forming lens 124 capable of changing a focusing state. The line sensor 125 is connected to an image processing unit 300 so as to output a signal corresponding to the intensity of light to be projected to each sensor unit.

Figure 2:
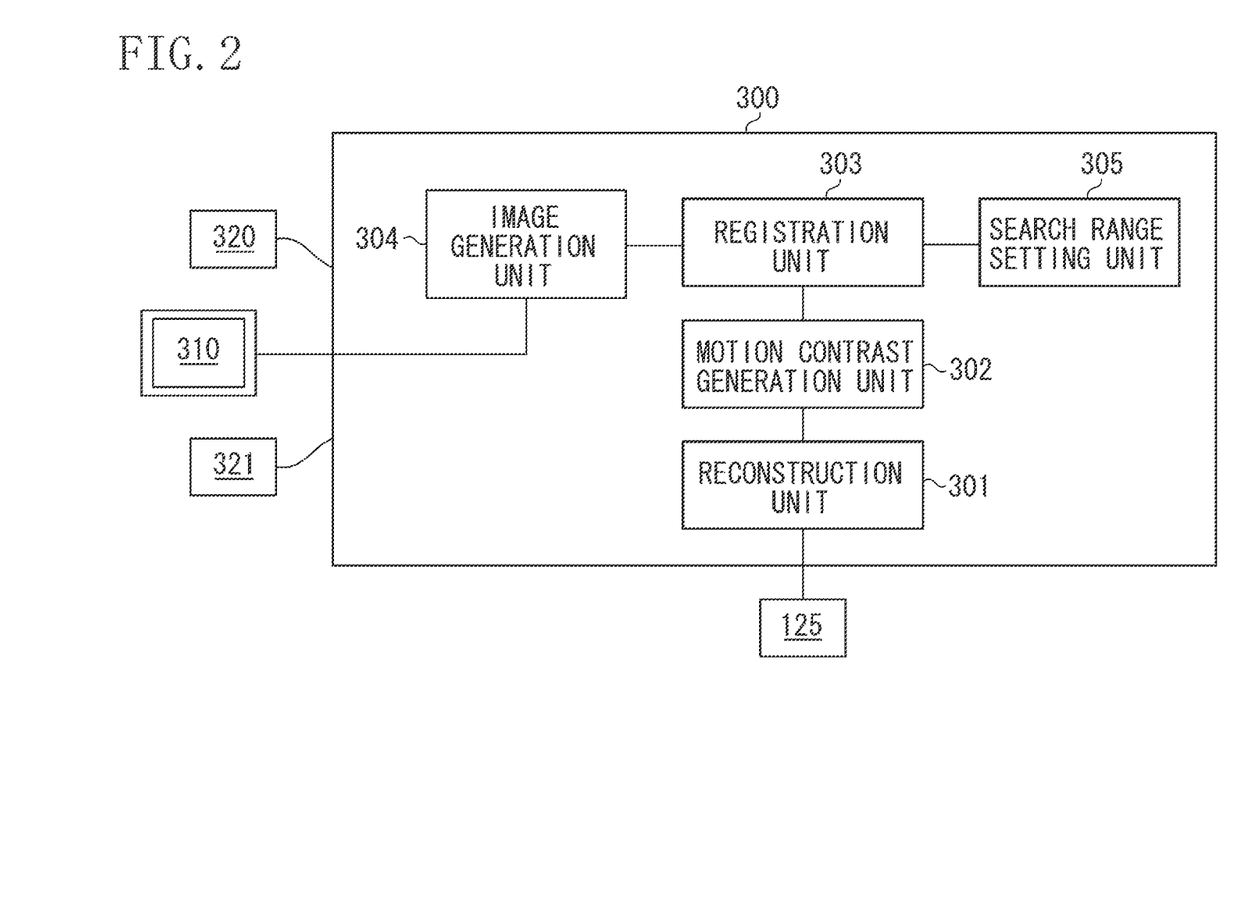
FIG. 2 is a block diagram illustrating a schematic configuration of an image processing unit according to the present exemplary embodiment.

FIG. 2 is a block diagram illustrating a schematic configuration of the image processing unit 300. As illustrated in FIG. 2, the image processing unit 300 includes a reconstruction unit 301, a motion contrast generation unit 302, a registration unit 303, an image generation unit 304, and a search range setting unit 305. In the present exemplary embodiment, the optical coherence unit 100 using the spectrum domain (SD) method is provided. The reconstruction unit 301 performs wavenumber transform and Fourier transform on output data from the line sensor 125 of the optical coherence unit 100, thereby generating tomographic image data on the eye to be examined. In the present exemplary embodiment, the optical coherence tomography apparatus that includes the optical coherence unit 100 using the SD method is used, but instead an apparatus including an optical coherence unit using the time domain (TD) method or the swept-source (SS) method may be used. The registration unit 303 performs registration of data on a plurality of generated tomographic images. The search range setting unit 305 sets a search range used for the registration unit 303 to perform registration. The motion contrast generation unit 302 generates motion contrast data from the registered data on the plurality of tomographic images. The image generation unit 304 generates an image for display from the generated tomographic image data or motion contrast data, and outputs the generated image to a monitor 310. The image processing unit 300 is connected to a pointing device 320 and a keyboard 321. The pointing device 320 is a mouse including a rotary wheel and a button, and is capable of specifying any position on the monitor 310. In the present exemplary embodiment, a mouse is used as the pointing device 320. However, any other pointing devices, such as a joystick, a touch pad, a trackball, a touch panel, and a stylus pen, may instead be used. As described above, the optical coherence tomography apparatus according to the present exemplary embodiment includes the optical coherence unit 100, the scanning optical system 200, and the image processing unit 300.

At least some of the parts of the image processing unit 300 may be implemented as independent devices. Alternatively, at least some of the parts of the image processing unit 300 may be implemented as software that is installed in one or more computers and executed by a central processing unit (CPU) of the corresponding one or more computers to thereby implement the functions of the parts. In the present exemplary embodiment, assume that each part is implemented by software and the software is installed in the same computer. The CPU controls the entire computer by using programs and data stored in a random access memory (RAM) or a read only memory (ROM). The execution of the software in each part is controlled to thereby implement the functions of each part. The RAM includes an area for temporarily storing programs and data loaded from a storage medium drive, and also includes a work area necessary for the CPU to perform various processes. The ROM generally stores programs, setting data, and the like for the computer. The image processing unit 300 may be configured as an electric circuit on an image processing board.

A control method for capturing a tomographic image of an eye to be examined by using the optical coherence tomography apparatus according to the present embodiment will now be described. First, an operator requests a patient, who is an examinee, to sit in front of the scanning optical system 200 and starts an OCT imaging operation after the alignment and input of patent information and the like. The light emitted from the light source 101 passes through the optical fiber 102a and is split by the light split unit 103 into measurement light, which travels toward the eye to be examined, and reference light, which travels toward the reflection mirror 113. The measurement light that travels toward the eye to be examined passes through the optical fiber 102b and is emitted from the end of the optical fiber 102b. Then, the measurement light is substantially collimated by the optical system 202 and is incident on the scanning unit 203. The scanning unit 203 includes galvanometer mirrors. The measurement light is deflected by the mirrors, passes through the lens 204, and irradiates the eye to be examined. The light reflected by the eye to be examined travels along the optical path in reverse and returns to the light split unit 103. Meanwhile, the reference light that travels toward the reference mirror passes through the optical fiber 102c and is emitted from the end of the optical fiber 102c. The reference light then passes through the collimate optical system 111 and the dispersion compensation optical system 112 and reaches the reflection mirror 113. The reference light reflected by the reflection mirror 113 travels along the optical path in reverse and returns to the light split unit 103.

The measurement light and the reference light that have returned to the light split unit 103 interfere with each other. The interference light enters the optical fiber 102d. The interference light is substantially collimated by the optical system 202 and then incident on the diffraction grating 123. The interference light that has entered the diffraction grating 123 forms an image on the line sensor 125 through the image forming lens 124, so that an interference signal at a single point on the eye to be examined can be obtained. The interference signal acquired by the line sensor 125 is output to the image processing unit 300. The interference signal output from the line sensor 125 is 12-bit integer data. The reconstruction unit 301 performs wavenumber transform, fast Fourier transform (FFT), and absolute value conversion (acquisition of an amplitude) on the 12-bit integer data, thereby generating tomographic image (A-scan) data in the depth direction at a single point on the eye to be examined.

After the interference signal at a single point on the eye to be examined is acquired, the scanning unit 203 drives the galvanometer mirrors so that interference light at another point adjacent to the point on the eye to be examined is generated. The interference light at the adjacent point passes through the line sensor 125 and the reconstruction unit 301, and the reconstruction unit 301 generates tomographic image data in the depth direction at the adjacent point on the eye to be examined. By repeating a series of these control processes, data (two-dimensional tomographic image data) on one tomographic image of the eye to be examined can be generated from a plurality of pieces of A-scan data. Further, the scanning unit 203 drives the galvanometer mirrors and scans the same portion (same scanning line) of the eye to be examined a plurality of times to thereby acquire data (two-dimensional tomographic image data) on a plurality of tomographic images at the same portion of the eye to be examined. Then, the scanning unit 203 drives the galvanometer mirrors to a small extent in the sub-scanning direction orthogonal to the main scanning direction, and acquires data (two-dimensional tomographic image data) on a plurality of tomographic images at another portion (adjacent scanning line) of the eye to be examined. By repeating these control process, data (three-dimensional tomographic image data) on a plurality of tomographic images in a predetermined range of the eye to be examined can be acquired.

The acquisition time interval for acquiring data on a plurality of tomographic images is determined depending on the acquisition rate of each A-scan and the number of pieces of A-scan data included in each piece of tomographic image data. For example, in the optical coherence tomography apparatus according to the present exemplary embodiment, the acquisition rate of each A-scan is 70,000 A-scans/second and the number of pieces of A-scan data included in each piece of tomographic image data is 232 to 696. After the acquisition of each tomographic image data, about 0.7 milliseconds are required as a time for returning the A-scan position to the head acquisition position of each tomographic image. Accordingly, the acquisition of each tomographic image is executed for an acquisition time in a range from about 4.0 milliseconds to 10.6 milliseconds. As the imaging view angle of each tomographic image, a width in a range from three millimeters to 10 millimeters can be set on the fundus. The number of pieces of A-scan data included in each piece of tomographic image data described above is variable. This is because the A-scan density is kept at a high density in a case where the imaging view angle of the OCTA is increased and an OCTA image with a wider angle of view and a higher image quality is obtained.

In the present exemplary embodiment described above, data on one tomographic image at a single point on the eye to be examined is acquired through FFT processing on a set of interference signals obtained from the line sensor 125. However, the interference signals may be divided into a plurality of groups and FFT processing may be performed on the divided interference signals so that data on a plurality of tomographic images can be obtained from one interference signal. According to this method, a larger number of pieces of tomographic image data than the number of scanning operations actually performed on the same portion of the eye to be examined can be obtained.

Figure 3:
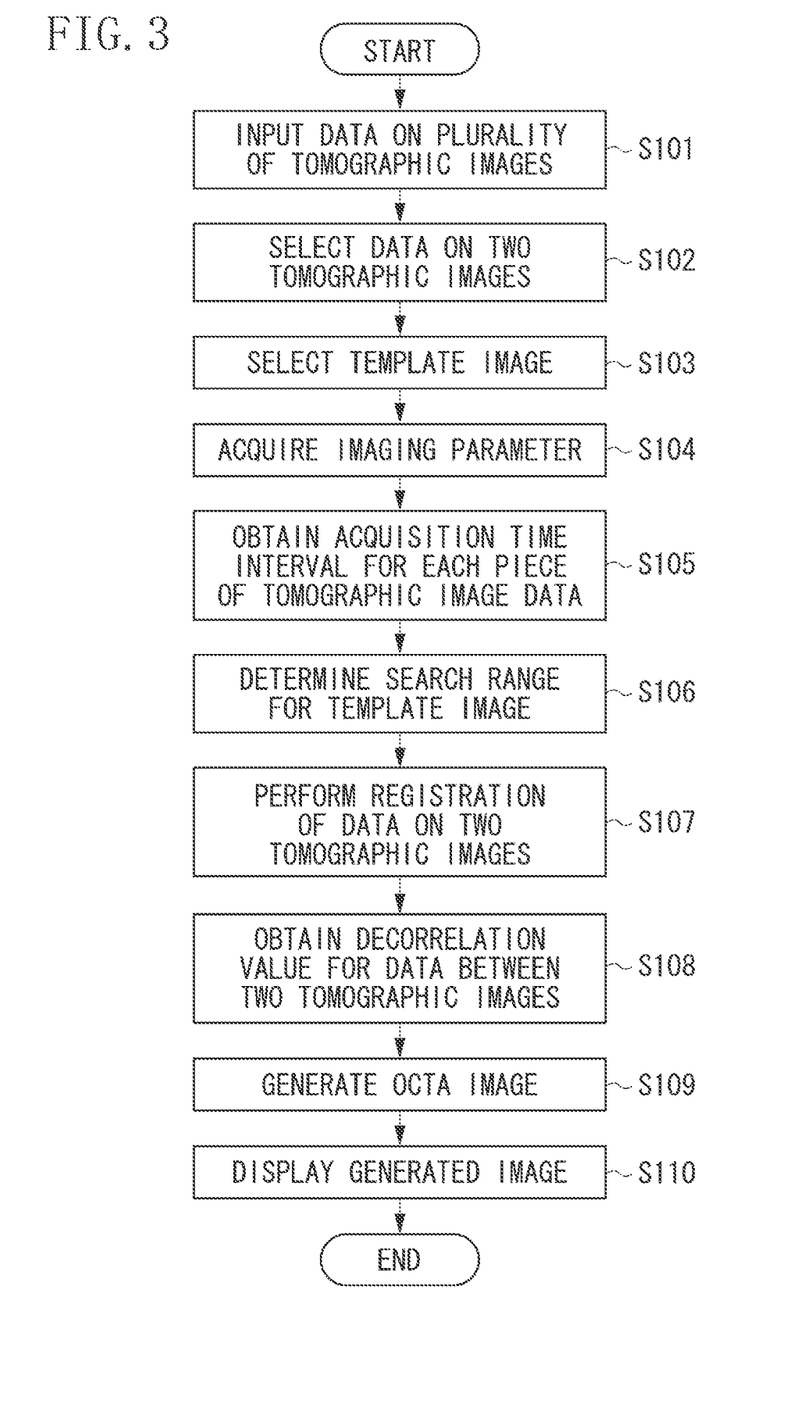
FIG. 3 is a flowchart illustrating a procedure for performing registration of a plurality of tomographic images according to the present exemplary embodiment.

A method for performing registration of data on a plurality of tomographic images in the optical coherence tomography apparatus will be described with reference to a flow-chart illustrated in FIG. 3. First, in step S101, data on a plurality of tomographic images generated by the reconstruction unit 301 is input to the registration unit 303. Next, in step S102, the registration unit 303 selects data on two tomographic images to be registered from the data on the plurality of tomographic images. The data on two tomographic images selected in this case is data on two tomographic images temporally adjacent to each other. For example, in a case where data on three tomographic images is successively acquired at the same scanning position, two tomographic images to be selected have combinations of "a first tomographic image and a second tomographic image"

or "a second tomographic image and a third tomographic image". This is because a blood flow within a predetermined rate range is extracted based on a variation in the images at a certain time interval. However, if a larger number of pieces of blood flow information is to be obtained by the addition of blood flows that are outside the predetermined rate range, data on two tomographic images which are not temporally adjacent to each other can also be selected. For example, a combination of "a first tomographic image and a third tomographic image" can also be used. In step S103, the registration unit 303 sets the entirety of one of the two selected tomographic images as a template image.

Meanwhile, the search range setting unit 305 sets a search range for searching for a position corresponding to the template image from the data on the other one of the tomographic images. Here, the template image is an example of a first tomographic image of the eye to be examined. The image different from the template image out of the two tomographic images is an example of a second tomographic image of the eye to be examined, where the second tomographic image is acquired at a time different from the time when the first tomographic image is acquired. In other words, the search range setting unit 305, which is an example of a determination unit, determines a search range for searching for the position corresponding to the first tomographic image in the second tomographic image. The search range may be a range for searching for a position corresponding to the other one of the tomographic images from the template image. In such a case, the template image is an example of the second tomographic image, and the other one of the images is an example of the first tomographic image.

In step S104, the search range setting unit 305, which is an example of the determination unit, acquires an imaging parameter for tomographic image data before the setting of the search range. The imaging parameter described herein is an example of the information about the acquisition time for acquiring tomographic images. Accordingly, the search range setting unit 305, which is an example of the determination unit, can determine the search range by using information about the acquisition time for acquiring tomographic images (e.g., the acquisition time interval for acquiring a plurality of tomographic images). The imaging parameter acquired in this case is an A-scan number NoA included in each tomographic image. Further, on the basis of the A-scan number NoA included in each tomographic image, the search range setting unit 305 sets a search range for the template image as follows. First, in step S105, the search range setting unit 305 obtains an acquisition time interval Tb for each piece of tomographic image data based on the A-scan number NoA included in the corresponding tomographic image.

$$Tb = \frac{NoA}{Ta} + Tr \quad (1)$$

In the formula (1), Ta represents an A-scan acquisition rate per unit time, and Tr represents a time required for returning the acquisition position to the head position after the acquisition of each tomographic image. The imaging parameter is substituted into the above formula (1), thereby obtaining the acquisition time interval Tb for acquiring each piece of tomographic image data. In this case, the acquisition time interval Tb for acquiring each piece of tomographic image data is obtained by the formula (1) using the imaging parameter, but instead the acquisition time interval Tb may be obtained by a simpler method. For example, a correspondence table between the A-scan number NoA and the acquisition time interval Tb may be prepared in advance to obtain the acquisition time interval Tb without the calculation described above.

Figure 4A:
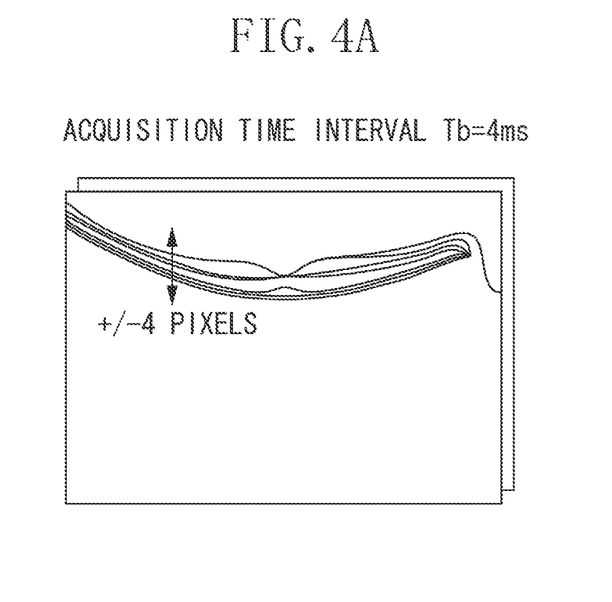
FIGS. 4A and 4B each illustrate a relationship between a tomographic image acquisition time interval and an eye moving amount according to the present exemplary embodiment.
Figure 4B:
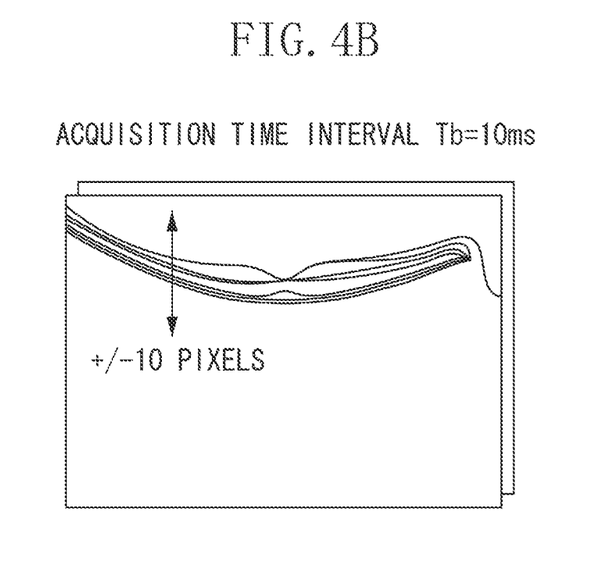

In step S106, the search range setting unit 305 determines a search range for the template image based on the acquisition time interval Tb. As described above, in the general OCTA imaging, the acquisition time interval Tb for acquiring each piece of tomographic image data is about several milliseconds to several tens of milliseconds, which is a relatively short time. Accordingly, it can be regarded that the motion of the eye to be examined within the acquisition time interval Tb is substantially constant. Thus, it can be said that the acquisition time interval Tb and the eye moving amount are substantially proportional. In addition, the search range setting unit 305 sets the search range based on the relationship between the acquisition time interval Tb and the motion of the eye. For example, as illustrated in FIG. 4A, when the acquisition time interval Tb is 4.0 milliseconds (A-scan number NoA is 232), the eye moving amount falls within about +/−4 pieces in a longitudinal direction on the tomographic image. In this case, as illustrated in FIG. 4B, when the acquisition time interval Tb is 10 milliseconds, it can be estimated that the eye moving amount falls within +/−10 pixels in the longitudinal direction on the tomographic image. The same holds true for the motion of the eye in a lateral direction on the tomographic image. Moreover, not only the motions in the longitudinal direction and the lateral direction, but also the motion of the inclination of the eye is included in the motion of the eye on the tomographic image. It is considered that this inclination is also substantially proportional to the acquisition time interval Tb. Accordingly, assuming that the positional deviation amount of the inclination of the eye falls within +/−10 in a case where the acquisition time interval Tb is 4.0 milliseconds, it is estimated that the positional deviation amount of the inclination of the eye falls within +/−2.5° in a case where the acquisition time interval Tb is 10 milliseconds. The optical coherence tomography apparatus according to the present exemplary embodiment uses the fact that the acquisition time interval Tb is substantially proportional to the motions in the longitudinal direction and the lateral direction on the tomographic image and the motion of the inclination. The search range setting unit 305 sets a search range Sy in the longitudinal direction on the tomographic image, a search range Sx in the lateral direction on the tomographic image, and a search range Sa for the inclination so as to be proportional to the acquisition time interval Tb.

As described above, a search with an unnecessarily wide range can be avoided by a search range for the template image being set on the basis of the acquisition time interval Tb, thus enabling rapid generation of an OCTA image. Further, the search range for the template image may be changed on the basis of the registration result previously obtained. For example, a search range smaller than the search range obtained by the method according to the present exemplary embodiment can be set for a patient with a small amount of positional deviation between a plurality of tomographic images in the previous OCTA imaging. Moreover, in a case where the search range obtained based on the acquisition time interval Tb exceeds a predetermined upper-limit value, it is desirable that the search range is set within the upper-limit value. This is because the moving amount of the eye to be examined often falls within a certain range even in a case where the acquisition time interval Tb is extremely long, and thus there is no need to perform a search with an unnecessarily wide range.

In step S107, the registration unit 303 moves the position of the template image and the inclination within the set search range and determines the longitudinal and lateral positions and inclination that best matches the other one of the tomographic images, thereby performing registration between two tomographic images. The inclination need not necessarily be obtained and one of a positional deviation in the longitudinal direction and a positional deviation in the lateral direction need not necessarily be obtained. For example, in the case of performing tracking through the control of an OCT scanning unit by using fundus front images acquired at different times (e.g., fundus images obtained by SLO, or front images generated using at least a part of OCT volume data), a positional deviation in the lateral direction can be reduced. Accordingly, a positional deviation in the longitudinal direction may be determined without obtaining a positional deviation in the lateral direction.

In the present exemplary embodiment, a decorrelation value which is a value obtained by subtracting a correlation value from 1 is used as an index for performing registration between the template image and the other one of the tomographic images. A decorrelation value for the other one of the tomographic images is determined by gradually shifting the longitudinal position, the lateral position, and the inclination position of the entire template image within the search range, thereby searching for a position where the decorrelation value is minimum. The position where the decorrelation value is minimum is used as the registration result. By using the decorrelation value for the registration as described above, it can be expected that the calculation of the decorrelation value during generation of motion contrast data can be omitted and the OCTA image can be rapidly generated. In the present exemplary embodiment, the decorrelation value is used as an index for registration between the template image and the other one of the tomographic images. Alternatively, a correlation value, a difference, a ratio, and the like can also be used instead of the decorrelation value. Here, the correlation value between tomographic images of a region corresponding to a blood flow is lower than that in the other regions. This is because a variation in the value becomes larger than that in the other regions due to the blood flow. Accordingly, in the case of generating motion contrast data corresponding to a blood flow, it is desirable to use the decorrelation value, which is a value obtained by subtracting a correlation value from 1, instead of using a correlation value. If a peak of an index value is not observed in the process of template matching, the registration may be performed again by increasing the search range. In step S108, the motion contrast generation unit 302 determines a decorrelation value through the following formula (2) for data between two tomographic images in which a positional deviation has been corrected.

$$Mxy = 1 - 2 \times \frac{Axy \times Bxy}{Axy^2 + Bxy^2} \quad (2)$$

In the formula (2), Axy represents an amplitude at a position (x, y) of tomographic image data A, and Bxy represents an amplitude at the same position (x, y) of tomographic image data B. The decorrelation value Mxy obtained as a calculation result takes values from 0 to 1. As the difference between two amplitude values increases, the decorrelation value Mxy becomes closer to 1. Further, a plurality of decorrelation values is obtained by repeating the decorrelation calculation described above by a number of times corresponding to the number of pieces of acquired tomographic image data, and an average value of the plurality of decorrelation values is obtained to thereby acquire final motion contrast data.

While the motion contrast data is determined based on the amplitude of complex data obtained after FFT processing in the present exemplary embodiment, the method for determining the motion contrast data is not limited to the method described above. The motion contrast data may be determined based on information about the phase of complex data, or may be determined based on information about the amplitude and the phase of complex data. Moreover, the motion contrast data may be obtained based on a real part and an imaginary part of complex data. While the motion contrast data is obtained through calculation of the decorrelation value between two values in the present exemplary embodiment, the motion contrast data may be obtained based on the difference between two values, or may be obtained based on the ratio between two values. While the average value of the plurality of acquired decorrelation values is determined in the present exemplary embodiment, the difference between the plurality of decorrelation values, or a maximum value of ratios between the plurality of decorrelation values may be determined as the final motion contrast data.

In step S109, the image generation unit 304 projects the motion contrast data on a two-dimensional plane in a predetermined depth range, thereby generating the final OCTA image. In step S110, the generated OCTA image is displayed on the monitor 310.

Figure 5:
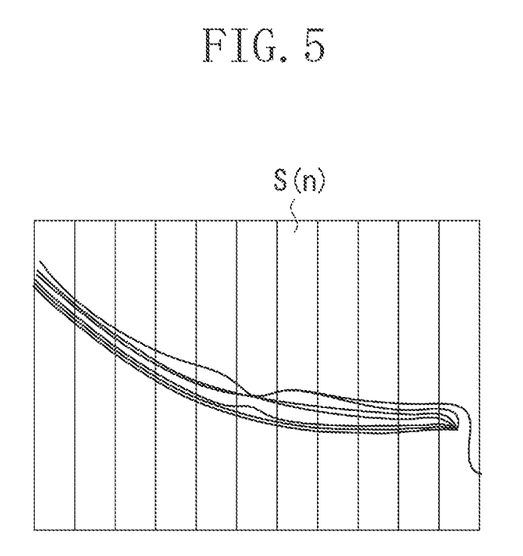
FIG. 5 illustrates an example where a tomographic image is divided into a plurality of vertically long thin rectangle regions according to the present exemplary embodiment.
Figure 6:
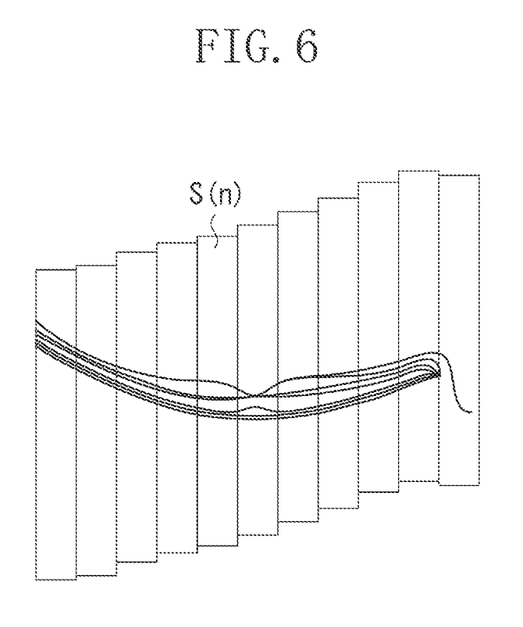
FIG. 6 illustrates an example of performing registration for each of the plurality of strip regions according to the present exemplary embodiment.

A second exemplary embodiment of the present invention will be described below in detail. The present exemplary embodiment differs from the first exemplary embodiment in that a search range for a template image is set based on the A-scan number NoA or an imaging view angle Ab so as to further speed up the processing of generating an OCTA image. Accordingly, descriptions of similar configurations are omitted. First, the registration unit 303 divides one of two selected tomographic images into a plurality of (n) vertically long thin rectangle regions S(n) as illustrated in FIG. 5, and sets the regions as a plurality of template images. Next, the search range setting unit 305 determines a search range in each template image based on the A-scan number NoA. In the present exemplary embodiment, the registration only in the longitudinal direction is performed on the tomographic image for each template image. Accordingly, only the search range Sy in the longitudinal direction is determined. Here, the registration in the lateral direction is omitted. This is because a scanning position is corrected through tracking in many optical coherence tomography apparatuses, and thus a positional deviation in the lateral direction is small. In the present exemplary embodiment, the registration of the thin rectangle regions S (n) in the longitudinal direction as illustrated in FIG. 6 makes it possible to correct a positional deviation in the inclination in a pseudo manner. Thus, the registration of the inclination can also be omitted. In the optical coherence tomography apparatus according to the present exemplary embodiment, the search range Sy in the longitudinal direction for each thin rectangle template image is determined by using the following formula (3):

$$Sy = \frac{NoA}{\alpha} - \beta \quad (3)$$

where α and β are constants.

In the formula (3), the search range Sy is set to be larger than an increase ratio of the A-scan number NoA, instead of increasing the search range in the longitudinal direction at the same ratio as the increase ratio of the A-scan number NoA. This is because the registration of the inclination is performed in a pseudo manner through registration of a plurality of thin rectangle regions in the longitudinal direction. It is considered that the amount of positional deviation in the longitudinal direction that is caused due to the inclination is proportional to the imaging view angle Ab. Accordingly, in the case of setting the search range Sy in the longitudinal direction, the search range Sy may be set so as to be proportional not only to the A-scan number NoA, but also to the imaging view angle Ab. Further, the registration unit 303 moves each of thin rectangle template images in the longitudinal direction within the obtained search range Sy in the longitudinal direction and determines the longitudinal position that best matches the other one of the tomographic images. If there is a positional deviation in the inclination, different registration results in the longitudinal direction are obtained for the respective thin rectangle template images. However, the registration of the entire image including the inclination can be performed through interpolation of the registration results. As described above, a search range in the longitudinal direction is set for a plurality of template images based on the A-scan number NoA and the imaging view angle Ab, thus enabling further speed-up of the OCTA image generation processing.

According to the first and second exemplary embodiments described above, a search range for each template image is set based on the acquisition time interval Tb, the A-scan number NoA, and the imaging view angle Ab so as to generate an OCTA image. These methods can also be applied to cases other than the case of generating an OCTA image. For example, in the case of acquiring a plurality of OCT tomographic images and performing averaging of the OCT tomographic images to obtain a high-quality OCT tomographic image, it is necessary to perform registration between a plurality of tomographic images. As a method for speeding up the registration processing, a search range for each template image can be set based on the acquisition time interval Tb, the A-scan number NoA, and the imaging view angle Ab.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-169295, filed Sep. 4, 2017, which is hereby incorporated by reference herein in its entirety.

What is claimed is:

1. An optical coherence tomography apparatus comprising:
    an interference optical system configured to acquire a tomographic image of an eye by using interference light between return light from the eye irradiated with measurement light and reference light corresponding to the measurement light;
    a determination unit configured to determine, by using information about an acquisition time for acquiring the tomographic image, a search range for searching for a position corresponding to a first tomographic image of the eye, the position being in a second tomographic image of the eye, and the second tomographic image having been acquired at a time different from a time when the first tomographic image is acquired; and
    a registration unit configured to perform registration of the first tomographic image and the second tomographic image by using information about the determined search range.

2. The optical coherence tomography apparatus according to claim 1,
    wherein the information about the acquisition time for acquiring the tomographic image is an acquisition time interval for acquiring a plurality of tomographic images of the eye at different times, and
    wherein the determination unit determines the search range in such a manner that the search range increases as the acquisition time interval becomes longer.

3. The optical coherence tomography apparatus according to claim 2, further comprising a scanning unit configured to scan the eye with the measurement light, wherein the acquisition time interval is an acquisition time for acquiring one tomographic image in a case where the tomographic image is acquired in both a forward path and a backward path for reciprocating scanning by the scanning unit.

4. The optical coherence tomography apparatus according to claim 2, further comprising a scanning unit configured to scan the eye with the measurement light, wherein in a case where a tomographic image is acquired in a forward path for reciprocating scanning by the scanning unit and no tomographic image is acquired in a backward path for the reciprocating scanning, the acquisition time interval is an acquisition time interval between acquisitions of two successive tomographic images and includes a travel time of the scanning unit from an end of one main scanning operation by the scanning unit to a start of a subsequent main scanning operation.

5. The optical coherence tomography apparatus according to claim 1, wherein the information about the acquisition time for acquiring the tomographic image indicates the number of pieces of A-scan data on one tomographic image, and the determination unit determines the search range in such a manner that the search range increases as the number of pieces of the A-scan data increases.

6. The optical coherence tomography apparatus according to claim 1,
   wherein the information about the acquisition time for acquiring the tomographic image indicates either one of a readout rate of a detection unit configured to detect the interference light and a swept source rate of a swept source light source, and
   wherein the determination unit determines the search range in such a manner that the search range increases as the rate decreases.

7. The optical coherence tomography apparatus according to claim 1, further comprising a scanning unit configured to scan the eye with the measurement light, wherein the information about the acquisition time for acquiring the tomographic image indicates a scanning rate and a scanning angle of the scanning unit.

8. The optical coherence tomography apparatus according to claim 1, wherein the registration unit performs the registration of the first tomographic image and the second tomographic image by correcting, for a plurality of regions elongated in a depth direction of the eye and set in the second tomographic image, a positional deviation between the first tomographic image and the second tomographic image in the depth direction of the eye.

9. The optical coherence tomography apparatus according to claim 1, further comprising a generation unit configured to generate motion contrast data by using the first tomographic image and the second tomographic image that have been subjected to the registration.

10. The optical coherence tomography apparatus according to claim 9,
    wherein the registration unit performs the registration of the first tomographic image and the second tomographic image by using information about the determined search range and a decorrelation value between the first tomographic image and the second tomographic image, and
    wherein the generation unit generates the motion contrast data by using the decorrelation value used for the registration.

11. The optical coherence tomography apparatus according to claim 1, wherein the registration unit performs the registration between the first tomographic image and the second tomographic image obtained by controlling the measurement light so that a substantially same position is repeatedly scanned with the measurement light by using information about the determined search range.

12. An image processing method comprising:
    acquiring a tomographic image of an eye by using interference light between return light from the eye irradiated with measurement light and reference light corresponding to the measurement light;
    determining, by using information about an acquisition time for acquiring the tomographic image, a search range for searching for a position corresponding to a first tomographic image of the eye, the position being in a second tomographic image of the eye, and the second tomographic image having been acquired at a time different from a time when the first tomographic image is acquired; and
    performing registration of the first tomographic image and the second tomographic image by using information about the determined search range.

13. A non-transitory computer-readable storage medium storing a program for causing a computer to execute the method according to claim 12.

* * * * *